United States Patent
Kumar et al.

(10) Patent No.: US 9,155,453 B2
(45) Date of Patent: Oct. 13, 2015

(54) EFFICIENT CONTINUOUS FLOW IRRIGATION ENDOSCOPE

(76) Inventors: Alka Kumar, Jaipur (IN); Atul Kumar, Jaipur (IN)

(*) Notice: Subject to any disclaimer, the term of this patent is extended or adjusted under 35 U.S.C. 154(b) by 1523 days.

(21) Appl. No.: 11/869,470

(22) Filed: Oct. 9, 2007

(65) Prior Publication Data

US 2008/0091074 A1   Apr. 17, 2008

(30) Foreign Application Priority Data

Oct. 11, 2006 (IN) .......................... 2236/DEL/2006

(51) Int. Cl.
| | | |
|---|---|---|
| *A61B 1/00* | (2006.01) | |
| *A61B 1/012* | (2006.01) | |
| *A61B 17/32* | (2006.01) | |
| *A61B 19/00* | (2006.01) | |
| *A61M 1/00* | (2006.01) | |

(52) U.S. Cl.
CPC .............. *A61B 1/012* (2013.01); *A61B 1/00071* (2013.01); *A61B 17/320016* (2013.01); *A61B 17/32002* (2013.01); *A61B 2019/5217* (2013.01); *A61B 2217/005* (2013.01); *A61B 2217/007* (2013.01); *A61M 1/0058* (2013.01)

(58) Field of Classification Search
CPC ........... A61B 1/00064; A61B 1/00135; A61B 1/00154; A61B 1/018; A61B 1/303; A61B 1/107
USPC ......... 600/105–107, 121–125, 153, 155–156, 600/158
See application file for complete search history.

(56) References Cited

U.S. PATENT DOCUMENTS

| | | | |
|---|---|---|---|
| 3,835,842 A | | 9/1974 | Iglesias |
| 4,203,444 A | * | 5/1980 | Bonnell et al. .................. 604/22 |
| 4,274,414 A | * | 6/1981 | Johnson et al. ................ 606/170 |
| 5,085,658 A | * | 2/1992 | Meyer ............................. 606/46 |
| 5,195,541 A | * | 3/1993 | Obenchain .................... 128/898 |
| 5,320,091 A | | 6/1994 | Grossi et al. |
| 5,392,765 A | | 2/1995 | Muller |
| 5,441,503 A | * | 8/1995 | Considine et al. ............. 606/115 |
| 5,456,689 A | * | 10/1995 | Kresch et al. ................. 606/180 |
| 5,486,155 A | | 1/1996 | Muller et al. |

(Continued)

FOREIGN PATENT DOCUMENTS

| | | |
|---|---|---|
| DE | 196 33 124 | 5/1997 |
| WO | WO-96/11638 | 4/1996 |
| WO | WO 99/11184 | 3/1999 |

*Primary Examiner* — Matthew J Kasztejna
(74) *Attorney, Agent, or Firm* — Dickstein Shapiro LLP

(57) ABSTRACT

A user friendly, safe and efficient continuous flow irrigation endoscope having only a single housing sheath without an inner sheath. The exclusion of the inner sheath increases the effective lumen of the endoscope. A long hollow cylindrical tube, capable of performing a to and fro and rotary motion, is placed inside the housing sheath to function as an endoscopic instrument, but also to serve as a conduit for evacuating waste fluid and detached tissue pieces present inside a tissue cavity. A single inflow port located at the proximal end of the single housing sheath allows the irrigation fluid to enter the tissue cavity via the lumen of the said housing sheath. The invented endoscope system has a single inflow port, a single outflow port, without an inner sheath so that all waste fluid and tissue debris present inside cavity are evacuated via the same single outflow port. No type of feedback mechanism, such as mechanical or electrical feedback mechanism, is incorporated in the endoscope to facilitate the removal of detached tissue pieces or waste fluid.

5 Claims, 1 Drawing Sheet

(56) References Cited

U.S. PATENT DOCUMENTS

| | | | |
|---|---|---|---|
| 5,498,258 A * | 3/1996 | Hakky et al. | 606/15 |
| 5,527,331 A * | 6/1996 | Kresch et al. | 606/170 |
| 5,536,234 A * | 7/1996 | Newman | 600/104 |
| 5,807,240 A | 9/1998 | Muller et al. | |
| 5,810,806 A * | 9/1998 | Ritchart et al. | 606/45 |
| 6,032,673 A * | 3/2000 | Savage et al. | 128/898 |
| 6,110,127 A | 8/2000 | Suzuki | |
| 6,113,594 A | 9/2000 | Savage | |
| 6,156,049 A | 12/2000 | Lovato et al. | |
| 6,159,209 A * | 12/2000 | Hakky | 606/45 |
| 6,402,715 B2 * | 6/2002 | Manhes | 604/35 |
| 6,645,140 B2 | 11/2003 | Brommersma | |
| 6,824,544 B2 | 11/2004 | Boebel et al. | |
| 7,249,602 B1 | 7/2007 | Emanuel | |
| 2003/0130565 A1 | 7/2003 | Muller | |
| 2003/0181906 A1 | 9/2003 | Boebel et al. | |
| 2006/0041186 A1 | 2/2006 | Vancaillie | |
| 2006/0047185 A1 | 3/2006 | Shener et al. | |
| 2006/0122459 A1 | 6/2006 | Aue | |

* cited by examiner

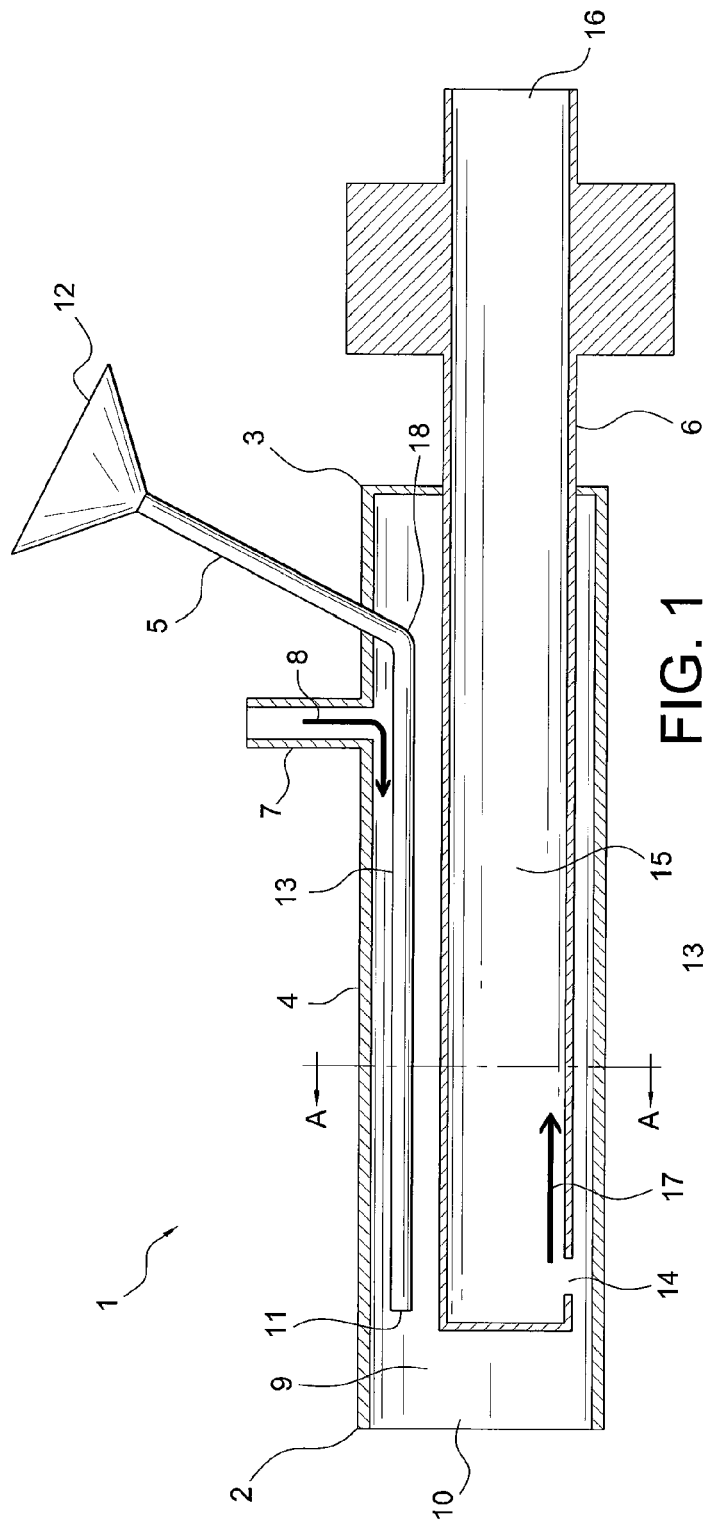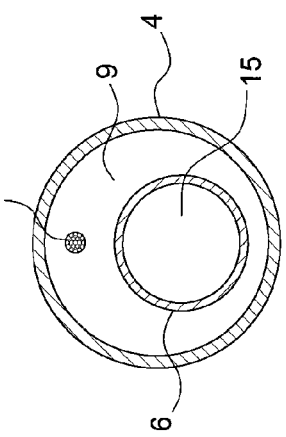

EFFICIENT CONTINUOUS FLOW IRRIGATION ENDOSCOPE

CROSS-REFERENCE TO RELATED APPLICATIONS

The present application claims the benefit of Indian Provisional Patent Application No. 2236/DEL/2006, filed on Oct. 11, 2006, the entire disclosure of which is incorporated by reference herein.

FIELD OF THE INVENTION

The present invention relates to surgeries and, in particular, to endoscopic procedures which deploy continuous flow irrigation, such as hysteroscopic fibroid morcellation, trans uretheral prostate morcellation, hysteroscopic polyp morcellation, hysteroscopic septoplasty, hysteroscopic adhesiolysis, trans uretheral morcellation of bladder tumors and arthroscopy.

BACKGROUND OF THE INVENTION

Continuous flow endoscopes are frequently used in endoscopic procedures such as hysteroscopy, trans uretheral urologic endoscopic procedures and arthroscopy. Those skilled in the art would know the structural composition of a continuous flow irrigation endoscope. In this application, the term "continuous flow irrigation" means that fluid simultaneously enters and escapes from a tissue cavity via separate entry and exit points, as a result of which positive fluid pressure is created inside the tissue cavity which distends the cavity. A continuous flow irrigation endoscope generally comprises an inner sheath which is placed inside the cylindrical lumen of an outer sheath. The sheaths are hollow cylindrical tubes which have a distal end which enters a tissue cavity, and a proximal end on which an inflow or outflow port is attached for the purpose of instilling or evacuating fluid from the cavity. The irrigation fluid is instilled via an inflow port.

In many prior art systems, the instilled fluid travels through the lumen of the inflow sheath and enters the tissue cavity via the distal opening of the inflow sheath. The waste fluid present inside the tissue cavity enters into a potential space present between the outer and the inner sheaths via multiple holes present near the distal end of the outer sheath and this waste fluid is finally evacuated via the outflow port attached at the proximal end of the outer sheath. A fiber optic telescope is placed inside the cylindrical lumen of the inner sheath, to view the interior of the tissue cavity. An endoscopic instrument can also be introduced via the lumen of the inner sheath. In this paragraph, the terms "outer sheath" and "inner sheath" refer to hollow cylindrical tubes which participate in maintaining the structural integrity of the endoscope, and such tubes also cannot move relative to each other. Also, the endoscopic instrument frequently moves relative to the outer and the inner sheaths. Various different types of "continuous flow irrigation endoscopes" have been described in U.S. Pat. Nos. 3,835,842; 5,320,091; 5,392,765; 5,807,240; and U.S. Patent Appln. Publ. Nos. 2003/0130565 A1 (Jul. 10, 2003); 2006/0041186 A1 (Feb. 23, 2006); and 2006/0122459 A1 (Jun. 8, 2006).

The arrangement described in the preceding paragraph has two major disadvantages which are negated by the system of the proposed invention. The disadvantages are as follows:

One disadvantage is that detached tissue pieces, larger than a critical size, present in the tissue cavity are unable to pass through the potential space between the outer and the inner sheaths. Thus, in endoscopic procedures the entire endoscope or the "endoscopic instrument" has to be repeatedly removed from the tissue cavity in order to evacuate the detached tissue pieces present inside the tissue cavity, and this increases the risk of complications like perforation, excessive bleeding and also increases the surgical time. As described in EP 0996375, U.S. Pat. No. 7,249,602 and U.S. Patent Appln. Publ. No. 2006/0047185, it may be argued that, instead of one outflow port, two outflow ports be installed via suitable mechanical means at suitable locations in the endoscope, one outflow port for primarily evacuating the waste fluid from the cavity and the other outflow port being meant to primarily evacuate the resected or cut tissue. However, such an arrangement is not desirable since it necessitates the incorporation of two out flow channels instead of one and it also tends to increase the overall weight of the endoscope. The system of the present invention solves all the problems described in this paragraph by utilizing only one single outflow port, attached to a single outflow channel, which serves to evacuate both detached tissue pieces and waste fluid from the tissue cavity in a continuous irrigation manner.

The other disadvantage is that the inner sheath, by virtue of occupying additional space, reduces the effective lumen diameter of the endoscope which necessitates a reduction in the thickness or size of the "endoscopic instrument" or the telescope or both. The system of the present invention reduces the problem mentioned in this paragraph by utilizing only one housing sheath and by utilizing special type of endoscopic instrument which additionally also functions as the sole outflow channel for simultaneously removing waste fluid and detached tissue pieces. In U.S. Pat. No. 6,824,544, waste fluid and tissue pieces are evacuated via an inflow sheath and the tissue is resected by a separate endoscopic instrument, loop, which cannot participate in removal of waste fluid or tissue pieces; both these features being contrary to the principals of the present invention.

Also, unlike U.S. Pat. No. 6,824,544, in the present invention, a single outflow channel (that is suction channel) is not bifurcated at the level of the endoscope and any type of valve, simple or solenoid operated, is not attached to the outflow channel. Also, unlike U.S. Pat. No. 6,824,544, in the present invention, a controller is not used for influencing or regulating the working of the endoscope, for example by way of controlling the opening and closing motion of solenoid valves. This paragraph describes requirements which essentially need to be fulfilled by the system of the present invention. These requirements have been imposed so that the use of the invented endoscope is not restricted to any specific type of fluid management system with a controller, so that only one outflow tube is needed to be connected to the endoscope, such that the endoscope is simple, light and user friendly.

In the present invention, the diameter or area of cross section of the inner lumen of a single outflow port needs to be at least equal to the diameter or area of cross section of the outflow channel, so that detached tissue pieces and waste fluid could be evacuated in the most efficient manner. Thus, in the present invention, unlike in EP 0996375, U.S. Pat. No. 7,249,602 and U.S. Patent Appln. Publ. No. 2006/0047185, a valve is not attached to the outflow channel for controlling the pressure or the fluid flow.

The present invention is essentially a continuous flow irrigation endoscope which cannot function if the single outflow channel is blocked, for example by an opening or closing valve. Thus, in the present invention, unlike in EP 0996375, U.S. Pat. No. 7,249,602 and U.S. Patent Appln. Publ. No. 2006/0047185, an opening or closing valve is not attached to the outflow channel.

OBJECT OF THE INVENTION

An object of the invention is to provide a continuous flow irrigation endoscope system in which the detached tissue pieces and waste fluid present inside a tissue cavity are evacuated in a continuous manner from the tissue cavity, without the need of removing the entire endoscope or a part of the endoscope from the tissue cavity.

Another object of the invention is to provide a continuous flow irrigation endoscope system in which both the detached tissue pieces and waste fluid are simultaneously evacuated in a continuous manner from the tissue cavity via a same single outflow port connected to a single outflow channel.

Another object of the invention is to provide a continuous flow irrigation endoscope system in which both the detached tissue pieces and waste fluid are simultaneously evacuated in a continuous manner from the tissue cavity via a same single outflow port, such that no mechanical or electrical feedback mechanism, or a valve of any type or a controller, is utilized for evacuating the detached tissue pieces or waste fluid.

Another object of the invention is to provide a continuous flow irrigation endoscope system to which only a single outflow tube needs to be connected.

Another object of the invention is to provide a continuous flow irrigation endoscope system in which the diameter or area of cross section of the inner lumen of the outflow port is at least equal to the diameter or area of cross section of the outflow channel.

Another object of the invention is to provide a continuous flow irrigation endoscope system which is relatively light in weight.

Another object of the invention is to provide a continuous flow irrigation endoscope system which is user friendly, safe and efficient.

BRIEF SUMMARY OF THE INVENTION

The present invention provides a continuous flow irrigation endoscope system in which both the waste fluid and tissue are removed from the tissue cavity via a same single outflow port. The system comprises a long hollow cylindrical tube open at both ends, the tube being placed inside the long cylindrical lumen of an outer housing sheath. The tube functions as an endoscopic instrument and also acts as a conduit for removing waste fluid and detached tissue from the tissue cavity. An inflow port is attached at the proximal end of the housing sheath for instilling fluid into a tissue cavity, while the proximal open end of the hollow cylindrical tube functions as an outflow port for the evacuation of detached tissue pieces and waste fluid.

The present invention also provides a method of conducting surgery employing a continuous flow irrigation endoscope system. The method comprises the steps of: providing a continuous flow irrigation endoscope system in the vicinity of a surgical site; and removing waste fluid and/or tissue debris from the surgical site with the endoscope, without utilizing any kind of a feedback mechanism or valve system to facilitate, affect or influence the evacuation or removal of tissue and/or waste fluid from the surgical site.

BRIEF DESCRIPTION OF THE DRAWINGS

FIG. 1 describes the basic layout of the invented system.

FIG. 2 is a cross-sectional view of the invented system of FIG. 1 taken along line A-A of FIG. 1.

DETAILED DESCRIPTION OF THE INVENTION

The present invention relates to a continuous flow irrigation endoscope in which the detached tissue pieces and waste fluid present inside a tissue cavity are automatically evacuated, in a continuous manner, without withdrawing the endoscope or any part of the endoscope from the tissue cavity.

The basic layout of the invented endoscope is shown in FIG. 1. The endoscope 1 has a distal end 2 which enters a tissue cavity and a proximal end 3 which lies outside the tissue cavity. The invented endoscope comprises an externally located "housing sheath" 4, an optical system 5 and a hollow cylindrical tube like instrument 6.

Again referring to FIG. 1, unlike many prior art systems, the invented system does not have a separate inner sheath, and a single sheath has been termed as "housing sheath" 4. The housing sheath 4 has an inflow port 7 located near its proximal end 3. Sterile irrigation fluid meant for distending a body tissue cavity is instilled via the inflow port 7 in the direction of the arrow 8. The irrigation fluid travels through the lumen 9 of the housing sheath 4 and finally enters the tissue cavity via a "distally located opening" 10 of the housing sheath 4. The cross section of the "distally located opening" 10 and or the cross section of the housing sheath 4 could also be oval in shape.

Again referring to FIG. 1, a hollow cylindrical tube like instrument 6 has been placed inside the lumen 9 of the housing sheath 4. For brevity, the hollow cylindrical tube like instrument 6 shall be referred to as "instrument" 6. The instrument 6 is a hollow cylindrical tube like structure having a distal opening 14, a lumen 15 and a proximally located opening which is being termed as the outflow port 16. The lumen diameter of the outflow port 16 is about the same as the lumen diameter of the rest of the instrument 6. The lumen diameter of the outflow port 16 could also be less than the lumen diameter of the rest of the instrument 6, but such an arrangement may retard the evacuation of detached tissue pieces. The waste fluid and the detached tissue pieces present inside the tissue cavity enter the lumen 15 of the instrument 6 through the distal opening 14 and travel in the direction of the arrow 17. The waste fluid and the detached tissue pieces are finally evacuated via the outflow port 16. Depending upon the surgical requirement, the cross section of lumen 15 could also be oval, or of any other shape.

As shown in FIG. 2, the effective cross sectional area of the housing sheath 4 should be preferably less than the effective cross sectional area of the instrument 6, as such an arrangement would facilitate the evacuation of detached tissue pieces. Here the term "effective cross sectional area" of the housing sheath 4 relates to the total cross sectional area of the housing sheath 4 from which the cross sectional area occupied by the instrument 6 and the optical channel 13 has been subtracted. The cross sectional area of the instrument 6 is denoted by the cross sectional area of the lumen 15 of the instrument 6.

The instrument 6 is placed inside the housing sheath 4 by virtue of a fluid tight contact. Also, those skilled in the art would know that generally an obturator is inserted inside the housing sheath subsequent to which the housing sheath is inserted into a tissue cavity. However, the obturator assembly has not been included in the drawing, for simplicity.

Again referring to FIG. 1, the optical system 5 comprises a telescope eyepiece 12 which is connectable to a video camera, an optical channel 13 which contains fiber optic bundles and a distal viewing tip 11 for visualizing the interior of the tissue cavity. In a exemplary embodiment, the optical channel 13 is not straight and has been deliberately provided with a bend 18. The optical channel 13 and the bend 18 are placed inside the lumen 9 of the housing sheath 4 and outside the lumen 15 of the instrument 6. In case the bend 18 is placed outside the lumen 9 of the housing sheath 4, then the fragile optical channel 13 could easily break at the bend 18. The bend 18 has been included to provide additional space for the instrument 6, especially if the instrument 6 is a hysteroscopic or urologic morcellator, or an arthroscopic shaver, in which cases additional space is needed to accommodate the driving mechanism of the morcellator or the shaver. The optical channel could also be straight but such an arrangement may not allow the incorporation of the said morcellator or a shaver. Also, the light source arrangement for the optical system 5 has not been included in FIG. 1 for simplicity.

Again referring to FIG. 1, the instrument 6 could be morcellator for hysteroscopic fibroid resection or for cutting a prostate adenoma in urologic endoscopic procedures. The instrument 6 could also be a shaver to be used in arthroscopic surgeries. The morcellator or the shaver have not been separately shown but the hollow inner channels of both are represented by the lumen 15 of the instrument 6. Also, those skilled in the art would understand that a window opening corresponding with the distal opening 14 is present near the distal end of hysteroscopic morcellators and shavers, wherein two cutting edges incorporated in two rotatable tubes facilitate tissue cutting in the region of the window. If the window is kept in the open position while the morcellator or the shaver is not operating, then the same would allow continuous flow irrigation all through the endoscopic procedure, that is, even while the morcellator or shaver is non functional. The instrument 6 could also be a simple cutting knife wherein the distal end of the instrument 6 would be required to be shaped like a conventional knife. The, knife could also function as a monopolar electrosurgical instrument. The instrument 6 could also be an electrode such as a ball electrode for ablating the endometrium, a prostate adenoma or a bladder tumor. The ball electrode, unlike the prior art ball electrodes, would have centrally placed a hollow cylindrical channel via which waste fluid and detached tissue generated during ablation could be evacuated.

Again referring to FIG. 1, and according to an exemplary embodiment only, it is important to note that instrument 6 may be configured to move in a to and fro direction relative to, and parallel to, the longitudinal axis of the housing sheath 4. The instrument 6 may be also capable of rotating around the longitudinal axis of the instrument 6 in either direction. Suitable mechanical means not shown in any FIGURE are deployed to facilitate the to and fro movement and the rotary movement of the instrument 6. The distal opening 14 of the instrument 6 may also be cut obliquely such that opening 14 is oval instead of being round.

Again referring to FIG. 1, the proximal part of the instrument 6 could also be provided with a "bend" similar to the bend 18 provided in the optical channel 13, and such bend could be located inside or outside the lumen 9 of the housing sheath 4. However, such an arrangement could retard the evacuation of detached tissue pieces.

Referring to FIG. 1, the relative locations of the optical channel 13 and the instrument 6 could even be interchanged with respect to each other or with respect to the inflow port 7.

Referring again to FIG. 1, the entire instrument 6, from the distal opening 14 to the proximally located outflow port 16, may comprise a metal, a rigid plastic material, a ceramic material, or a combination of the same, for example.

The outlet of instrument 6 has been termed as "outflow port" 16 only for sake of an easier description. In the prior art continuous flow endoscopes, the term "outflow port" is commonly referred to an outlet attachment which is attached at the proximal end of an outer or an inner sheath. Also, in the prior art systems the sheaths are immovable relative to each other, they do not function as an instrument, their purpose being only to provide structural integrity to the endoscope and to provide channels for instilling or removing fluid from a tissue cavity. However, in the present invention the so-called "outflow port" is attached at the proximal end of the movable instrument 6, the instrument not being meant to impart structural integrity to the endoscope; the instrument can also be replaced by a different type of instrument depending upon the surgical requirement.

Referring to FIG. 1, it is also important to note that no feedback mechanism, no valves and no valve-like system have been provided anywhere in the endoscope 1 for facilitating, affecting or influencing the evacuation of detached tissue pieces and waste fluid in any manner. It is important to note that the proximal end of the instrument 6 has not been bifurcated in any manner. This means that the outlet port 16 is connectable to only a single outflow tube 33 which would transport the detached tissue pieces and the waste fluid to a waste collecting container 30 shown in any FIG. 1. The outflow tube may be made of flexible resilient polymeric material. If at all any bifurcation, valve system or a feedback mechanism, as explained in this paragraph, needs to be installed, then the same could be installed only in the outflow tube, sufficiently away from the endoscope 1, such that the installation does not enhance the weight of the endoscope because "low weight" of the endoscope is one of the objectives of the invention.

In the preceding paragraphs, it might be misinterpreted that the instrument 6 is primarily meant to act as an outflow channel for evacuating waste fluid and detached tissue pieces from a tissue cavity. However, the primary aim of the instrument 6 is to act as an endoscopic instrument while the hollow cylindrical lumen 15 of the instrument 6 simply provides a passage for the evacuation of detached tissue pieces and waste fluid.

The invention is useful because it allows evacuation of detached tissue pieces present in a tissue cavity during endoscopic procedures deploying continuous flow irrigation, and without the need of withdrawing the endoscope or a part of the endoscope from the tissue cavity.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A continuous flow endoscope, comprising:
   a single tubular housing sheath without a separate inner sheath, the single housing sheath having a longitudinal axis, a distal end and a proximal end, the single housing sheath being tubular along its entire length, the single housing sheath having a circular inner cross section;
   an optics channel located within the single housing sheath, the optics channel having a bent region which forms an angle with the longitudinal axis of the single housing sheath;

a movable tube located at least partially within the single housing sheath, the movable tube being configured to cut tissue and evacuate the cut tissue through the movable tube of the endoscope, the movable tube having a hollow cylindrical lumen that provides a passage for evacuation of waste fluid and detached tissue pieces present in a tissue cavity during an endoscopic procedure deploying continuous flow irrigation, the entire movable tube being configured to move in both a linear motion and a rotary motion relative to the longitudinal axis of the single tubular housing sheath, wherein the movable tube is a morcellator provided with a morcellator window and is configured to directly cut intact living tissue of a tissue cavity of a patient by virtue of the morcellator window being in direct apposition with the intact living tissue of the patient and evacuate the cut tissue, and wherein the movable tube is also a conduit for removing waste fluid and detached tissue from the tissue cavity;

a single inflow port located at the proximal end of the single housing sheath configured to allow fluid to enter the single housing sheath, the inflow port being formed on an outer circumferential portion of the single housing sheath and in contact with the single housing sheath; and a single outflow port located at a most proximal end of the movable tube and located outside the single housing sheath so that the entire waste fluid and cut tissue is directly evacuated via same single outflow port, the outflow port being connectable to a single outflow tube, and wherein the area of cross section of an inner lumen of the single outflow port is at least equal to or greater than the area of cross section of an inner lumen of the movable tube;

wherein the single housing sheath has an effective cross sectional area less than an effective cross sectional area of the movable tube, wherein the effective cross sectional area of the single housing sheath is the total cross sectional area of the housing sheath from which the cross sectional area occupied by the movable tube and the optical channel has been subtracted and the effective cross sectional area of the movable tube is the cross sectional area of the lumen of the movable tube, such that the continuous flow endoscope does not necessitate a feedback mechanism or a valve system for removal of waste fluid, cut tissue or debris.

2. The endoscope of claim 1, wherein the angle is about 45 degrees.

3. The endoscope of claim 1, wherein the bent region is located within the single housing sheath.

4. The endoscope of claim 1, wherein about 75% of the movable tube is located within the single housing sheath.

5. The endoscope of claim 1, wherein the movable tube has a cross-section which is circular, oval or elliptical.

* * * * *